US011173130B2

(12) United States Patent
Ilios

(10) Patent No.: US 11,173,130 B2
(45) Date of Patent: Nov. 16, 2021

(54) DRUG DELIVERY SYSTEM AND METHODS OF USE

(71) Applicant: Massachusetts Eye and Ear Infirmary, Boston, MA (US)

(72) Inventor: Eleftherios Paschalis Ilios, Quincy, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 15/760,699

(22) PCT Filed: Sep. 23, 2016

(86) PCT No.: PCT/US2016/053284
§ 371 (c)(1),
(2) Date: Mar. 16, 2018

(87) PCT Pub. No.: WO2017/053686
PCT Pub. Date: Mar. 30, 2017

(65) Prior Publication Data

US 2018/0250239 A1 Sep. 6, 2018

Related U.S. Application Data

(60) Provisional application No. 62/232,143, filed on Sep. 24, 2015.

(51) Int. Cl.

| | |
|---|---|
| ***A61K 9/70*** | (2006.01) |
| ***C07K 16/24*** | (2006.01) |
| ***A61K 47/34*** | (2017.01) |
| ***A61K 47/30*** | (2006.01) |
| ***A61K 9/06*** | (2006.01) |
| ***A61K 47/32*** | (2006.01) |
| *A61K 39/00* | (2006.01) |

(52) U.S. Cl.
CPC .............. *A61K 9/7007* (2013.01); *A61K 9/06* (2013.01); *A61K 9/70* (2013.01); *A61K 47/30* (2013.01); *A61K 47/32* (2013.01); *A61K 47/34* (2013.01); *C07K 16/241* (2013.01); *A61K 2039/505* (2013.01); *A61K 2039/545* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 4,148,839 A * | 4/1979 | Fydelor | C08J 7/16 525/10 |
| 7,192,629 B2 | 3/2007 | Lammertink et al. | |
| 7,972,628 B2 * | 7/2011 | Ratner | A61L 27/14 424/499 |
| 8,206,450 B2 | 6/2012 | Henry et al. | |
| 8,409,606 B2 | 4/2013 | Sawhney et al. | |
| 2002/0086977 A1 * | 7/2002 | Lai | C07K 17/08 530/350 |
| 2005/0003007 A1 | 1/2005 | Boix et al. | |
| 2006/0110429 A1 | 5/2006 | Reiff et al. | |
| 2006/0182783 A1 | 8/2006 | Hughes et al. | |
| 2007/0191938 A1 | 8/2007 | Hossainy | |
| 2012/0059462 A1 | 3/2012 | Wong | |
| 2013/0195952 A1 | 8/2013 | Byrne et al. | |
| 2014/0050739 A1 * | 2/2014 | Francois | A61K 45/06 424/158.1 |
| 2014/0322327 A1 * | 10/2014 | Laukkanen | A61K 9/0034 424/488 |
| 2015/0037422 A1 | 2/2015 | Kaplan et al. | |

FOREIGN PATENT DOCUMENTS

| | | | |
|---|---|---|---|
| WO | WO 2004/106435 | | 12/2004 |
| WO | WO2013126799 | * | 8/2013 |
| WO | WO2014044704 | * | 3/2014 |

OTHER PUBLICATIONS

Mattiason et al., Macroporous Polymers: Production Properties and Biotechnological/Biomedical Applications, Dec. 2009, https://books.google.com/books?id=WxHJMITc4vOC&dq=%22monodisp+ersed+pores%22+and+%22drug+delivery%22&lr=& source=gbs_navlinks_s (Year: 2009).*
Aburahma and Mahmoud, "Biodegradable ocular inserts for sustained delivery of brimonidine tartarate: preparation and in vitro/in vivo evaluation," AAPS PharmSciTech, 2011, 12(4):1335-47.
Ako-Adounvo et al., "Recent patents on ophthalmic nanoformulations and therapeutic implications," Recent Pat Drug Deliv Formul, 2014, 8(3):193-201.
Antao et al., "Stabilization of Bilateral Progressive Rheumatoid Corneal Melt with Infliximab," Case Reports in Ophthalmological Medicine, 2012, 2012(72):I-3.
Cade et al., "Alkali burn to the eye: protection using TNF-α inhibition," Cornea, 2014, 33(4):382-9.
Dastjerdi et al., "Corneal Penetration of Topical and Subconjunctival Bevacizumab," Invest Ophthalmol Vis Sci, 2017, 52(12):8778-23.
Dastjerdi et al., "Topical bevacizumab in the treatment of corneal neovascularization results of a prospective, open-label, noncomparative study," Arch Ophthalmol, 2009, 124 (4); 381-9.
Dohlman et al., "Boston Keratoprosthesis in Stevens-Johnson Syndrome: A case of using infliximab to prevent tissue necrosis," Digital Journal of Ophthalmology, 2009, 15[1):I-6.

(Continued)

*Primary Examiner* — Jennifer A Berrios
(74) *Attorney, Agent, or Firm* — Fish & Richardson P.C.

(57) ABSTRACT

A drug delivery system (DDS) including a hydrophobic porous scaffold and a hydrogel having a hydrophilic polymer and one or more biologic drugs provides sustained zero-order release of the one or more biologic drugs. Also provided herein are methods of making and using a DDS including a hydrophobic porous scaffold and a hydrogel having a hydrophilic polymer and one or more biologic drugs.

21 Claims, 10 Drawing Sheets

(56) References Cited

OTHER PUBLICATIONS

Dohlman et al., "Corneal blindness from end-stage Sjögren's syndrome and graft-versus-host disease," In: Sullivan D, Stern M Tsubota K et al., eds. Lacrimal Gland, Tear Film, and Dry Eye Syndromes 3, New York: Kluwer / Plenum Publishers, 2002:7335-8.
Ferrari et al., "Safety and Efficacy of Topical Infliximab in a Mouse Model of Ocular Surface Scarring," Invest Ophthalmol Vis Sci, Mar. 2013, 54: 1680-88.
Ferrari et al., "Tumor Necrosis Factor-a Inhibitors as a Treatment of Corneal Hemangiogenesis and Lymphangiogenesis," Eye Contact Lens, 2014.
Guzman-Aranguez et al., "Contact lenses: promising devices for ocular drug delivery," J Ocul. Pharmacol Ther, 2013, 29(2):189-99.
Hu et al., "Bevacizumab in the treatment of pterygium: a meta-analysis," Cornea, Feb. 2014, 33: 154-60.
Ikeda et al., "Stability of infliximab in polyvinyl chloride bags," American Journal of Health-System Pharmacy, 2012, 69(17):1509-12.
International Preliminary Report on Patentability in International Application No. PCT/US2016/053284, dated Apr. 5, 2018, 9 pages.
International Search Report and Written Opinion in International Application No. PCT/US2016/053284, dated Dec. 7, 2016, 16 pages.
Jain and Singh, "Harms of TNF inhibitors in rheumatic diseases: a focused review of the literature," Immunotherapy, 2013, 5(3):265-99.
Jansen Biotech, Remicade prescribing information. Secondary Remicade prescribing information, 2013, http://www.remicade/shared/product/remicade/prescribing-information.pdf. 21 pages.
Kim and Chung, "The effect of topical infliximab on corneal neovascularization in rabbits," Cornea, 2013, 32(2J:185-90.
Leibovich et al., "Macrophage-induced angiogenesis is mediated by tumour necrosis factor-alpha," Nature, 1987, 329(6140):630-2.
Li et al., "Effectiveness of topical infliximab in a mouse model of experimental dry eye," Cornea, 2012, 31Suppl 1:525-31.
Li et al., "Regulation of MMP-9 Production by Human Corneal Epithelial Cells," Experimental Eye Research, 2001, 73(4): 449-59.
Mashak and Rahimi, Silicone Polymers in Controlled Drug Delivery Systems: A Review, Iranian Polymer Journal, 2009, 18: 279-295.
Odorcic et al., "Infliximab for the treatment of refractory progressive sterile peripheral ulcerative keratitis associated with late corneal perforation: 3-year follow-up," Cornea, 2009, 28(7):89-92.
Paschalis et al., "Removal of Silicone Oil From Intraocular Lens Using Novel Surgical Materials," Tran Vis Sci Tech, 2014, 3(5):4.
Pham et al., "Use of infliximab in the treatment of peripheral ulcerative keratitis in Crohn disease," Am I Ophthalmol 2011, 152(2):783-8.e2.
Robert et al., "Stability and in vitro toxicity of an infliximab eye drop formulation," International Journal of Pharmaceutical Compounding, 2014, 18(5):418-26.
Seet et al., "Cerebrovascular events after bevacizumab treatment: an early and severe complication," Neurocrit Care, 2011, 15(3):421-7.
Thomas and Pflugfelder, "Therapy of progressive rheumatoid arthritis-associated corneal ulceration with infliximab," Cornea, 2005, 24(6):742-4.
Turgut et al., "Topical infliximab for the suppression of wound healing following experimental glaucoma filtration surgery," Drug Des Devel Ther, 2014, 2(B):42L-9.
Vashist and Ahmad, "Hydrogels: Smart Materials for Drug Delivery," Oriental Journal of Chemistry, 2013, 29: 861-870.
Vassileva and Hergeldzhieva, "Avastin use in high risk corneal transplantation," Graefes Arch Clin Exp Ophthalmol, 2009, 247(12):1.70L-6.

* cited by examiner

FIGs. 10A-B
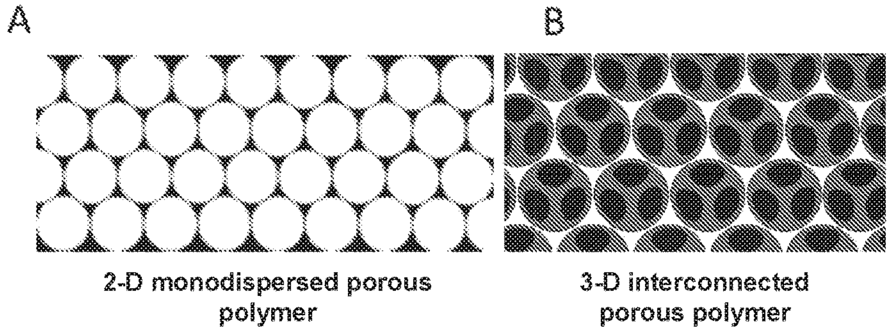
FIG. 11
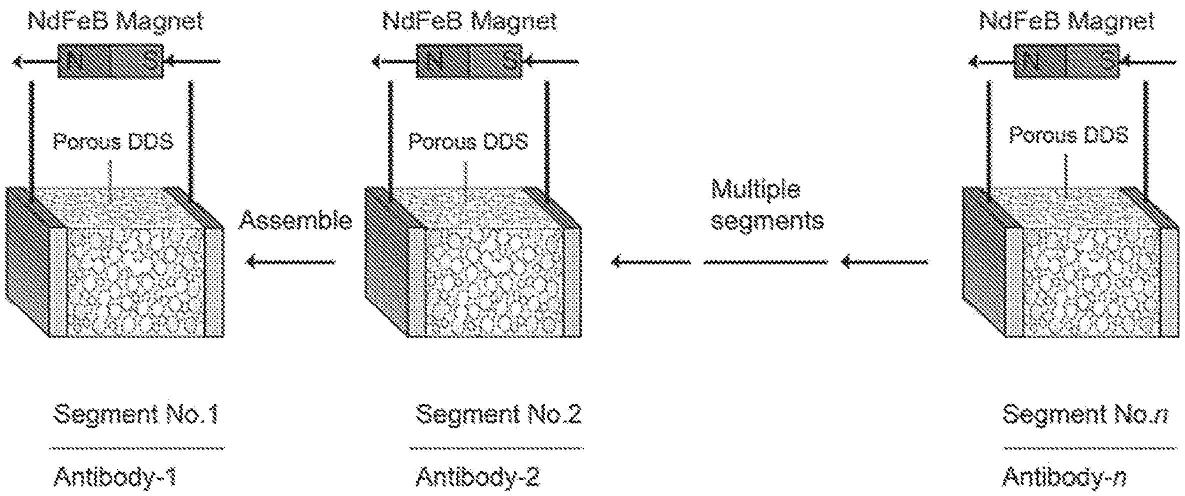

DRUG DELIVERY SYSTEM AND METHODS OF USE

CLAIM OF PRIORITY

This application is a 371 U.S. National Phase Application of PCT/US2016/053284, filed on Sep. 23, 2016, which claims the benefit of U.S. Provisional Patent Application Ser. No. 62/232,143, filed on Sep. 24, 2015, the entire contents of which are hereby incorporated by reference.

TECHNICAL FIELD

This disclosure relates to materials and methods for sustained zero-order drug delivery of biologic drugs.

BACKGROUND

Biologic agents targeting key cytokines and growth factors are being applied to an expanding spectrum of human systemic diseases and ocular disorders, but carry a high risk of significant systemic adverse events (Seet et al., 2011 *Neurocrit Care* 15 (3):421-7; Jain and Singh, 2013 *Immunotherapy* 5 (3):265-99; and Jansen Biotech, Dec. 16, 2014 *Remicade Product Monograph*). Systems have been developed for sustained drug delivery to the ocular surface. For example, colloidal formulations such as liposomes and nanoparticles can be designed to improve corneal penetration and drug stability (Ako-Adounvo et al., 2014 *Recent Pat Drug Deliv Formul* 8 (3):193-201), but these thicker formulations may cause visual blurring by adhering on the corneal surface upon instillation, which in turn, may harm patient compliance. Contact lenses have also been used for the release of several therapeutic agents including antibiotics and glaucoma drugs (Guzman-Aranguez et al., 2013 *J Ocul Pharmacol Ther* 29 (2):189-99), but the needs of optical clarity, oxygen permeability, and specific design for fit over the cornea, limit the types of materials and the degree of customization. Dissolvable inserts have also been used (Aburahma et al., 2011 *AAPS PharmSciTech* 12 (4):1335-47), but drug release and dissolution of these inserts are dependent on hydration and tear flow, which may be highly variable in patients.

SUMMARY

Provided herein are materials and methods for providing localized, sustained zero-order drug delivery of one or more biologic drugs (e.g., anti-TNF-α antibody). Local administration of biologic drugs requires lower doses than systemic administration, thus minimizing costs and the risk of systemic complications.

Provided herein are drug delivery systems. The drug delivery systems can have a porous 3-dimensional hydrophobic polymer scaffold and a hydrogel including a hydrophilic polymer and one or more biologic drugs. The porous scaffold can include polydispersed pores 100-300 μm in diameter. In some aspects, the hydrophobic polymer including a silicon-based polymer (e.g., PDMS). In some aspects, the hydrophilic polymer can include poly(vinyl alcohol) (PVA) (e.g., a PVA having a MW of 85,000-124,000 Da). In some aspects, the one or more biologic drugs can include at least one of an anti-vascular endothelial growth factor (VEGF) agent or an anti-tumor necrosis factor alpha (TNF-α) agent. The hydrogel can include 5 mg/ml of the one or more biologic drugs. The drug delivery system can be about 5×2×1 mm in size. The drug delivery system can be sterilized using gamma-irradiation (e.g., 25 KGy).

Also provided herein are methods of using drug delivery systems. The methods include administering to a patient a drug delivery system having a porous 3-dimensional hydrophobic polymer scaffold and a hydrogel comprising a hydrophilic polymer and one or more biologic drugs. The patient can be a human. The administering can be non-invasive. The drug delivery system can be administered a topical surface (e.g., a lower eyelid fornix).

In some aspects, the methods provide sustained zero-order release of one or more biologic drugs to a patient and can include administering to a patient a drug delivery system having a porous 3-dimensional hydrophobic polymer scaffold and a hydrogel comprising a hydrophilic polymer and one or more biologic drugs. Sustained release can include an extended time period of 1 month. The release of one or more biologic drugs can include a release of at least 70% of the one or more biologic drugs. The release of the one or more biologic drugs can occur at 2.5 ng/mL/day.

In some aspects, the methods provide localized delivery of one or more biologic drugs to a patient and can include administering to a patient a drug delivery system having a porous 3-dimensional hydrophobic polymer scaffold and a hydrogel including a hydrophilic polymer and one or more biologic drugs. Localized delivery of one or more biologic drugs can be effective to treat an eye disease (e.g., macular degeneration, diabetic macular edema, corneal neovascularization, pterygium, high-risk penetrating keratoplasty, corneal alkali burn, neurotrophic keratopathy, dry eye, and glaucoma).

In some aspects, the methods can be used to treat an eye disease in a patient and can include administering to a patient a drug delivery system having a porous 3-dimensional hydrophobic polymer scaffold and a hydrogel comprising a hydrophilic polymer and one or more biologic drugs. The eye disease can include a topical disease of the eye or ocular inflammation (e.g., glaucoma, corneal neovascularization, pterygium, high-risk penetrating keratoplasty, neurotrophic keratopathy, dry eye, alkali burn, and anterior uveitis).

In some aspects, the methods can improve eye graft and/or keratoprosthesis retention in a patient and can include administering to a patient a drug delivery system having a porous 3-dimensional hydrophobic polymer scaffold and a hydrogel comprising a hydrophilic polymer and one or more biologic drugs. The eye graft can be a keratoplasty (e.g., penetrating keratoplasty, lamellar keratoplasty, Boston keratoprosthesis, AlphaCor implantation, and osteo-odonto-keratoprosthesis).

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 10A-B are images showing pore dispersion. A) Monodispersed cavitation arrangement in a 2-D representation. B) A cross-section 3-D representation of a monodispersed cavity interconnected with other cavities.

FIG. 11 is a schematic showing assembly of a drug delivery system having multiple DDS segments with different biologic agents connected with magnetic force.

DETAILED DESCRIPTION

Figure 1:
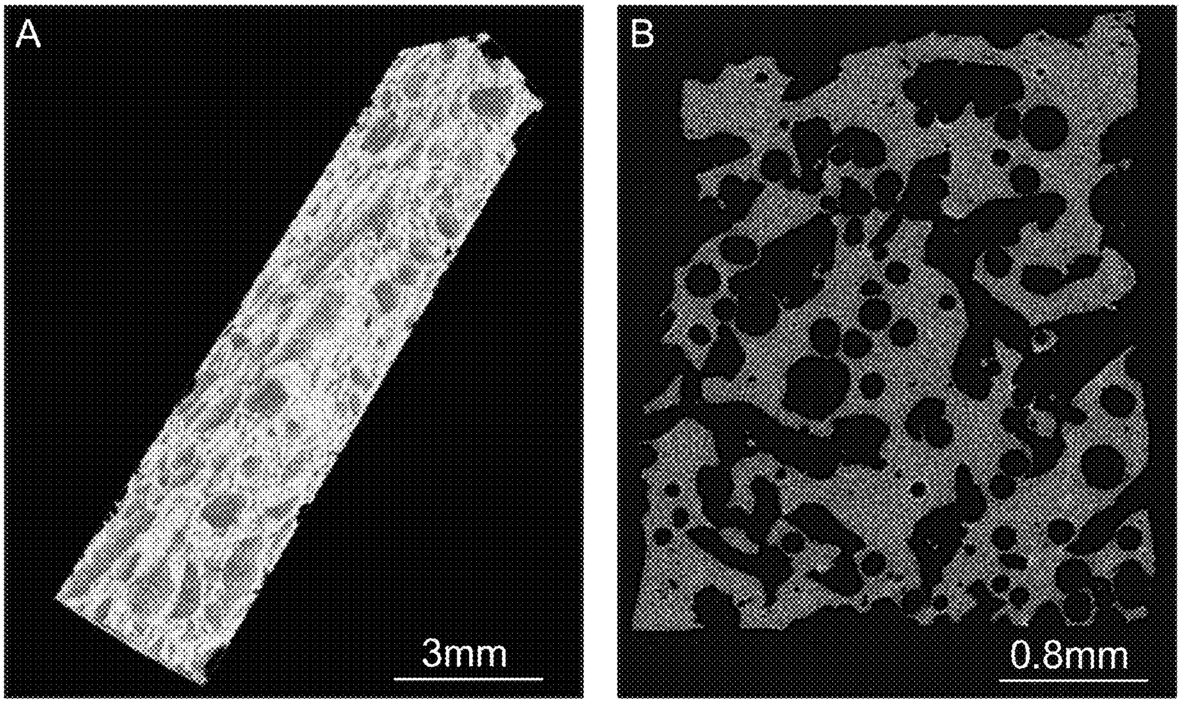
FIGS. 1A-B shows X-Ray microtomography of the porous polydispersed polydimethylsiloxane (PDMS). A) Macroscopic and B) microscopic appearance of porous PDMS. The microstructure of PDMS was determined using non-destructive, molybdenum-generated radial x-ray scans. Three-dimensional image reconstruction of the micro-computed-tomography (μCT) (X-Tek HMXST225, Nikon Metrology Inc., Brighton, Mich., USA) was achieved using VGStudio Max 2.2 image reconstruction software (Volume Graphics, Heidelberg, Germany). The porous cavities are subsequently loaded with infliximab using polyvinyl alcohol as a loading polymer.

This disclosure provides materials and methods for local, sustained delivery of one or more biologic drugs. Local administration achieves lower systemic exposure to the drug and therefore is likely associated with lower rates of severe adverse events. The sustained and selective release of biologics to localized tissue has several advantages, e.g., maximizing bioavailability and minimizing side effects.

Drug Delivery Device

Provided herein is a drug delivery system (DDS) including a hydrophobic polymer scaffold and a hydrogel having a hydrophilic polymer and one or more biologic drugs.

As used herein, a "polymer" is a compound formed by covalently linking smaller molecules termed "monomers" into a covalently bonded chain. The monomers present in a polymer molecule can be the same or different. If the monomers are the same, the polymer may also be called a homopolymer. If the monomers are different, the polymer may also be called a copolymer. Polymers can be linear or branched. A polymer can be obtained from a commercial source or be synthesized from the polymerization of a desired monomer or combination of different monomers. Methods of polymer synthesis are well known in the art.

A DDS can be used to deliver one or more biologic drugs via invasive or non-invasive methods to any topical surface or tissue. In some embodiments, a DDS is used to deliver one or more biologic drugs via non-invasive methods to a topical surface. For example, a DDS can be used to deliver one or more biologic drugs to the skin, the nostrils, the lips of the mouth, the eye, the ears, the trachea, the stomach, the genital area, or the anus. In some embodiments, a DDS is used to deliver one or more biologic drugs to the eye. For delivery of one or more biologic drugs to the eye, a DDS can be placed, for example, at the conjunctival fornix (e.g., the lower eyelid fornix), or implanted under the conjunctiva. For intraocular delivery the DDS can be placed in the anterior chamber or the vitreous cavity.

A DDS can be any shape and/or size. The size and shape of a DDS can be determined according to the site of administration, the time for administration, and/or the concentration of biologic drug required to be administered. The shape of a DDS can be described in terms of 2-dimensional shapes (e.g., circle, ellipse, triangle, quadrilateral, square, rectangle, pentagon, hexagon, etc.). The shape of a DDS can be described in terms of 3-dimensional shapes (e.g., sphere, torus, cylinder, cone, cube, cuboid, pyramid, prism, etc.). In some embodiments, a DDS is a millimeter-scale device. Each dimension (height, width, and depth) can independently be about 0.05 mm to 1000 mm (i.e., 100 cm) in length. For example, each dimension of a DDS can independently be about 0.05 mm, about 0.1 mm, about 0.5 mm, about 1.0 mm, about 1.2 mm, about 2 mm, about 5 mm, about 10 mm, about 15 mm, about 30 mm, about 50 mm, about 75 mm, about 100 mm, about 200 mm, about 500 mm, or about 1000 mm in length. For example, a DDS can be about 1000×200×1 mm in size. For example, a DDS can be about 5×2×1 mm in size.

A DDS provided herein can include one or more segments. Two or more segments can be combined as needed.

In some embodiments, for non-invasive delivery of one or more biologic drugs to the eye, a DDS having a size of 5×2×1 mm can be placed at the lower eyelid fornix.

Scaffold

A DDS provided herein includes a hydrophobic polymer scaffold. In some embodiments, the scaffold is a three-dimensional (3-D) porous hydrophobic polymer scaffold. A porous hydrophobic polymer scaffold provides a cavitation volume. For example, a porous hydrophobic polymer scaffold can have at least 10% cavitation volume, e.g., at least 20% cavitation volume, at least 30% cavitation volume, at least 40% cavitation volume, at least 50% cavitation volume, at least 60% cavitation volume, at least 70% cavitation volume, at least 80% cavitation volume, or at least 90% cavitation volume. The cavitation volume allows the scaffold to be loaded with the hydrogel. For example, a porous hydrophobic polymer scaffold can hold at least 1% w/v hydrogel, e.g., at least 5% w/v hydrogel, at least 10% w/v hydrogel, at least 15% w/v hydrogel, at least 20% w/v hydrogel at least 25% w/v hydrogel at least 30% w/v hydrogel at least 40% w/v hydrogel at least 50% w/v hydrogel, or at least 60% w/v hydrogel. In some embodiments, a porous hydrophobic polymer scaffold can hold at least 50% w/v hydrogel.

A hydrophobic polymer scaffold can have pores of any size. The pore size can be customized as described herein in order to customize the release kinetics of one or more biologic drugs from the DDS. In some embodiments, the porous scaffold includes pores about 0.1-500 μm in diameter. In some embodiments, the porous scaffold includes pores about 100-300 μm in diameter. As used herein, the term diameter means the longest dimension of the pore. The pores can be designed to be monodispersed or polydispersed (see, e.g., FIG. 10). In some embodiments, the pores are polydispersed.

In some embodiments, a DDS provided herein can include one or more segments. For example, each segment can include the same pore size or different pore size. Two or more DDS segments (e.g., each containing different pore size) can be combined as needed.

In some embodiments, a DDS includes a 3-D porous PDMS scaffold having pores about 100-300 μm in diameter.

Any hydrophobic polymer can be used for the scaffold. Hydrophobic polymers are non-polar, rendering them soluble in non-polar solvents and insoluble in polar solvents. In some embodiments, a hydrophobic polymer is biocompatible. In some embodiments, a hydrophobic polymer is a silicon-based polymer (i.e., a polysiloxanes). Suitable silicone-based hydrophobic polymers may include any siloxane such as, without limitation, polydimethylsiloxane (PDMS), polyhydromethylsiloxane (PHMS), polymethylphenylsiloxane (PMPhS), fluorosilanes, and copolymers of silicone-acrylates, polyether polysiloxane and fluorinated acrylates.

In some embodiments a hydrophobic polymer includes PDMS. PDMS is a chemical compound having the repeating unit $[Si(CH_3)_2O]_n$ where n may be any real number (e.g., a whole number). Polymers are typically characterized by molecular weight (MW). For example, "PDMS60" typically denotes a preparation that includes a mixture of oligomers having an average MW of 60 kDa. In some embodiments, PDMS may have an average MW of about 60 to about 120 kDa.

In some embodiments, a DDS includes a 3-D porous hydrophobic PDMS polymer scaffold having a cavitation volume of at least 80% cavitation volume and pores about 100-300 μm in diameter, and can hold at least 50% w/v hydrogel.

Hydrogel

A DDS provided herein includes a hydrogel having a hydrophilic polymer and one or more biologic drugs. As used herein a "hydrogel" is a network of hydrophilic polymers as a gel in which water is the dispersion medium.

Any hydrophilic or amphiphilic polymer can be used for the hydrogel. In some embodiments, a hydrophilic or amphiphilic polymer is biocompatible. Hydrophilic polymers contain polar or charged functional groups, rendering them soluble in water. Amphiphilic polymers contain both hydrophilic and lipophilic properties. Without being limited by theory, it is believed that the hydrophilic polymers easily suspend one or more biologic drugs (e.g., antibodies) which are hydrophilic in nature. Suitable hydrophilic polymers may include, without limitation, poly(ethylene glycol) (PEG), poly(ethylene oxide) (PEO), polyoxyethylene (POE), poly(N-isopropylacrylamide) (PNIPAM), polyacrylamide (PAM), poly(2-oxazoline), polyethylenimine (PEI), poly(acrylic acid), polymethacrylate and other acrylic polymers, poly(vinyl alcohol) (PVA) and copolymers, and poly (vinylpyrrolidone) (PVP), polylactic-co-glycol acid (PLGA), chitosan/alginate, and copolymers.

In some embodiments, a hydrophilic polymer includes PVA. PVA is a chemical compound having the repeating unit $[CH_2CH(OH)]_n$ where n may be any real number (e.g., a whole number). Polymers are typically characterized by molecular weight (MW). For example, "PVA85000" typically denotes a preparation that includes a mixture of oligomers having an average MW of 85,000 kDa. In some embodiments, PVA may have an average MW of about 10,000 to about 200,000 kDa. For example, PVA may have a MW of at least 10,000 ($PVA_{10000}$), at least 20,000 ($PVA_{20000}$), at least 30,000 ($PVA_{30000}$), at least 40,000 ($PVA_{40000}$), at least 50,000 ($PVA_{50000}$), at least 60,000 ($PVA_{60000}$), at least 70,000 ($PVA_{70000}$), or at least 80,000 ($PVA_{80000}$). For example, PVA may have a MW of no greater than 200,000 ($PVA_{200000}$), no greater than 190,000 ($PVA_{190000}$), no greater than 180,000 ($PVA_{180000}$), no greater than 170,000 ($PVA_{170000}$), no greater than 160,000 ($PVA_{160000}$), or no greater than 150,000 ($PVA_{150000}$) kDa.

In some embodiments, the hydrophilic polymer includes PVA having a MW of about 85,000-about 124,000 kDa.

One or more biologic drugs are dispersed within the hydrophilic polymer. A "biologic drug" or a "biologic" as used herein is any medicinal or therapeutic product manufactured in, extracted from, or synthesized from a living organism (e.g., a human, animal, microorganism or plant). For example, a biologic drug can include one or more of an antibody, a peptide, a polysaccharide, a lipid, a nucleic acid, or any combination thereof. A biologic drug can be isolated from a natural source or synthesized. In some embodiments, a biologic drug includes an antibody.

Any biologic drugs can be used. In some embodiments, a biologic drug is effective to treat a topical eye disease. For example, a biologic drug (e.g., anti-VEGF) can be effective to treat macular degeneration and/or diabetic macular edema (e.g., by preventing or reducing choroidal neovascularization), and ocular surface conditions such as corneal neovascularization, pterygium, and high-risk penetrating keratoplasty. For example, a biologic drug (e.g., anti-TNF-α) can be effective to treat corneal alkali burn (e.g., by reducing corneal opacity, perforation, eyelid fibrosis, inflammation, and/or neovascularization, and/or by inhibiting retinal ganglion cell layer apoptosis), dry eye (e.g., by improving tear volume, corneal surface regularity, and/or goblet cell density), and/or glaucoma (e.g., by preventing or reducing corneal neovascularization and/or by suppressing subconjunctival wound healing after trabeculectomy). For example, a biologic drug (e.g., a neurotrophin such as a brain derived neurotrophic factor and/or a ciliary derived neurotrophic factor) can be effective for corneal reinnervation.

For example, one or more biologic drugs can include anti-vascular endothelial growth factor (VEGF) agents (e.g., ranibizumab and/or bevacizumab), anti-tumor necrosis factor alpha (TNF-α) agents (e.g., infliximab and/or etanercept), anti-IL-1β agents (e.g., gevokizumab), IL-1 receptor antagonist (e.g., anakira), neurotrophins (e.g., brain-derived neurotrophic factor (BDNF)). In some embodiments a biologic drug is anti-TNF-α. In some embodiments, one or more biologic drugs comprise at least one of an anti-VEGF agent or an anti-TNF-α agent.

Any amount of one or more biologic drugs can be loaded in the hydrophilic polymer. The specific dose of any particular biologic drug will, of course, be determined by the particular circumstances of the individual patient including the size, weight, age and sex of the patient, the nature and stage of the disease being treated, the aggressiveness of the disease, and the route of administration of one or more biologic drugs. In some embodiments, a hydrophilic polymer can be loaded with (i.e., the hydrogel contains) about 0.1 mg/ml of one or more biologic drugs to about 100 mg/ml or one or more biologic drugs. For example, a hydrophilic polymer can be loaded with about 0.1 mg/ml of one or more biologic drugs, about 0.5 mg/ml of one or more biologic drugs, about 1 mg/ml of one or more biologic drugs, about 2 mg/ml of one or more biologic drugs, about 5 mg/ml of one or more biologic drugs, about 10 mg/ml of one or more biologic drugs, about 15 mg/ml of one or more biologic drugs, about 20 mg/ml of one or more biologic drugs, about 35 mg/ml of one or more biologic drugs, about 50 mg/ml of one or more biologic drugs, about 65 mg/ml of one or more biologic drugs, about 80 mg/ml of one or more biologic drugs, or about 100 mg/ml of one or more biologic drugs. In some embodiments, a hydrophilic polymer can be loaded with (i.e., the hydrogel contains) about 5 mg/ml anti-TNF-α antibody.

In some embodiments, a DDS provided herein can include one or more segments. For example, each segment can include the same polymers or different polymers. Two or more DDS segments (e.g., each containing different polymers) can be combined as needed. In embodiments having more than one biologic drug, the biologic drugs can be loaded in the same segment or in different segments. Two or more DDS segments (e.g., each containing different polymers or each containing different biologic drugs) can be combined as needed.

In some embodiments, a DDS includes a hydrogel having PVA hydrophilic polymer loaded with 5 mg/mL anti-TNF-α antibody.

Drug Release

A DDS can be used to administer one or more biologic drugs described herein with sustained zero-order release. As used herein, sustained release includes release of the one or more biologic drugs for an extended time period. Without being limited by theory, it is believed that the hydrogel releases the one or more biologic drugs only by the activation of the polymer with a fluid (e.g., a body fluid). Release kinetics of a one or more biologic drugs from a DDS can be determined as described in Example 1.

Delivery of one or more biologics for an extended period of time eliminates the need for systemic administration or repeated topical injections. An extended time period can include at least 1 week, at least 2 weeks, at least 3 weeks, or at least 4 weeks. An extended time period can include at least 1 month, at least 2 months, at least 3 months, at least 4 months, at least 5 months, or at least 6 months. In some embodiments, an extended time period includes at least 1 month.

Delivery of one or more biologics for an extended period of time can also include an initial burst of release followed by zero-order release. A burst can include the first minutes to first day of the extended time period. For example, a burst can last for about 1 hour, about 2 hours, about 3 hours, about 4 hours, about 5 hours, about 6 hours, about 7 hours, about 8 hours, about 9 hours, about 10 hours, about 11 hours, about 12, hours, about 13 hours, about 14 hours, about 15 hours, about 16 hours, about 17 hours, about 18 hours, about 19 hours, about 20 hours, about 21, hours, about 22 hours, about 23 hours, or about 24 hours of the extended time period.

Release of one or more biologic drugs from a DDS is a complete release. As used herein "complete release" means all or nearly all (e.g., at least 70%) of the one or more biologic drugs loaded in the hydrogel is released from the DDS. For example, complete release of one or more biologic drugs can include release of 100%, release of at least 99%, release of at least 98%, release of at least 97%, release of at least 96%, release of at least 95%, release of at least 94%, release of at least 93%, release of at least 92%, release of at least 91%, release of at least 90%, release of at least 89%, release of at least 88%, release of at least 87%, release of at least 86%, release of at least 85%, release of at least 84%, release of at least 83%, release of at least 82%, release of at least 81%, release of at least 80%, release of at least 79%, release of at least 78%, release of at least 77%, release of at least 76%, release of at least 75%, release of at least 74%, release of at least 73%, release of at least 72%, release of at least 71%, release of at least 70% of the one or more biologic drugs.

In embodiments where the extended period of time includes an initial burst of release, the burst can release a high dose of one or more biologic drugs initially followed by zero-order release. A burst can release up to 80% of the one or more biologic drugs loaded in the hydrogel from the DDS. For example, a burst can release at least 1%, at least 5%, at least 10%, at least 20%, at least 30%, at least 40%, at least 50%, at least 60%, at least 70%, at least 80% of the one or more biologic drugs. A burst can release one or more biologic drugs at an initial rate of release of about 1 μg/mL/day to about 10 μg/mL/day. In some embodiments, a burst release rate can be about 4.2 μg/mL/day.

Zero-order release of one or more biologic drugs can occur at any rate of release provided the rate remains constant. The combination of a hydrophobic polymer scaffold and a hydrogel having a hydrophilic polymer and one or more biologic drugs provides control over drug release kinetics. In some embodiments, a zero-order release rate can be about 1 ng/mL/day to about 10 ng/mL/day. In some embodiments, a zero-order release rate can be about 2.5 ng/mL/day.

In embodiments having different hydrogel segments, each segment can provide independent release kinetics. For example, a first hydrogel segment can release the one or more biologic drugs at a first rate of release and a second hydrogel segment can release the one or more biologic drugs at a second rate of release. Two or more segments of hydrogel with different release kinetics of a biologic drug can be combined as needed.

In some embodiments, a DDS can provide complete zero-order release of anti-TNF-α for about 1 month.

Stability

The hydrogel provides stability to typically unstable biologic drugs (e.g., antibodies). Whether a biological drug is stable can be determined as described in Example 1.

A DDS described herein can be stored (and provide stability of any suspended biologic drug) for at least 1 year. For example, a DDS can be stored for at least 1 day, at least 2 days, at least 3 days, at least 4 days, at least 5 days, at least 6 days, or at least 7 days. For example, a DDS can be stored for at least 1 week, at least 2 weeks, at least 3 weeks, or at least 4 weeks. For example, a DDS can be stored for at least 1 month, at least 2 months, at least 3 months, at least 4 months, at least 5 months, at least 6 months, at least 7 months, at least 8 months, at least 9 months, at least 10 months, at least 11 months, or at least 12 months.

A DDS can be stored at any temperature. Suitable storage conditions include freezers (about −20° C. to about −80°), refrigerators (about 4° C.), room temperature (about 20-26° C.), and body temperature (about 37° C.). In some embodiments, a DDS described herein can be stored at about 37° C. for at least 1 month. In some embodiments, a DDS described herein can be stored at about 4° C. for at least 1 year. In some embodiments, a DDS described herein can be stored at about 20-26° C. for at least 1 year.

The stability provided to one or more biologic drugs by a DDS described herein enables post fabrication sterilization. For example, a DDS described herein can be sterilized using gamma-irradiation. Sterilization can be done without adverse effects on the biological affinity of any biologic drug and without adverse effects on the kinetics of a DDS. For example, gamma-irradiation at about 2, about 5, about 10, about 12, about 15, or about 25 KGy can be used to sterilize a DDS without adverse effects on the biological affinity of any biologic drug and without adverse effects on the kinetics of the DDS. In some embodiments, a DDS described herein can be sterilized using 25 KGy gamma irradiation.

In some embodiments, a sterilized DDS can be stored at 4° C. or 20-26° C. for at least a year.

Methods of Making

Provided herein are methods of making a DDS including a hydrophobic polymer scaffold and a hydrogel having a hydrophilic polymer and one or more biologic drugs. Typically, a hydrophobic polymer scaffold and a hydrogel having a hydrophilic polymer and one or more biologic drugs are made independently and then the hydrogel is loaded into the hydrophobic polymer scaffold.

A hydrophobic polymer scaffold can be made using any known technique. Suitable techniques for making 3-D scaffolds include, without limitation, 3-D printing, soft lithography, inverse 3-D lithography, inverse opal fabrication, femtosecond laser ablation, 2 photons 3-D photoresist cross-linking, and/or multi-photon UV multi-stack layer lithography with photoresist.

In some embodiments, a hydrophobic polymer scaffold is made using inverse 3-D fabrication with sacrificial particles as known in the art and described, for example, in Paschalis et al. (2014 *Tran Vis Sci Tech.* 3 (5):4). A particle dissolvable in a polar solvent (e.g., water, isopropanol, toluene or high temperature or etchant) provides a negative template for a porous hydrophobic polymer. Suitable water, isopropanol, toluene or, etchant dissolvable particles include, without limitation, monosaccharides (e.g., arabinose, xylose, ribose, allose, glucose, dextrose, mannose, galactose, fructose, etc.), disaccharides (e.g., sucrose, lactose, sucralose, etc.), or resins. Suitable temperature dissolvable particles may include polystyrene, polymethylmethacrylate (PMMA), silicon dioxide, titanium silicates, copper oxides, manganese oxide, titania or zirconia. Dissolvable particles can be any size and/or shape, with the size and/or shape determining the size and/or shape of the pores in the hydrophobic polymer scaffold. In some embodiments, a dissolvable particle has a longest dimension of about 10-500 μm. In some embodiments, a dissolvable particle has a longest dimension of about 100-300 μm.

In some embodiments, a hydrophobic polymer scaffold can be made as described in Example 1. Briefly, a 3-D porous scaffold can be made by laying sucrose particles on a silicone (Si) wafer, sonicating, placing PDMS flexible silicon elastomer over the sucrose particles, degassing in a vacuum chamber, and curing the mixture. The sucrose template is then dissolved with water leaving a 3-D porous PDMS block. See also, for example, FIG. 2 (steps 1-4).

A hydrogel having a hydrophilic polymer and one or more biologic drugs can be made using any known technique. For example, a hydrophilic polymer described herein can be dissolved in water (e.g., DI water) and combined with one or more biologic drugs described herein.

In some embodiments, a hydrogel can be made as described in Example 1. Briefly, PVA powder can be added into DI water until dissolved, and anti-TNF-α antibody is suspended in the PVA solution at a 34:1 weight/volume ratio.

The hydrogel can be loaded into a hydrophobic polymer scaffold by any means. Suitable means of loading a hydrogel into a hydrophobic polymer scaffold include, without limitation, applying vacuum, and high pressure flow through the polymer.

In some embodiments, a hydrogel can be made as described in Example 1. Briefly, a hydrogel is loaded into a hydrophobic polymer scaffold using a vacuum chamber. See also, for example, FIG. 2 (steps 4-5).

In embodiments including one or more biologic drugs, different biologic drugs can be loaded in different DDS segments and multiple segments can be combined in a single hydrogel, as shown in FIG. 11. For example, a first DDS segment can be loaded with a first biologic drug and a second DDS segment can be loaded with a second biologic drug. Two or more segments of DDS with different biologic drugs can be combined as needed.

Methods of making a DDS including a hydrophobic polymer scaffold and a hydrogel having a hydrophilic polymer and one or more biologic drugs can also include sterilization. Any suitable method of sterilization can be used. For example, a DDS described herein can be sterilized using gamma-irradiation. In some embodiments, a DDS described herein can be sterilized, e.g., using gamma irradiation, e.g., at 25 KGy.

Methods of Using

Provided herein are methods of using a DDS including a hydrophobic polymer scaffold and a hydrogel having a hydrophilic polymer and one or more biologic drugs. For example, the methods provided herein provide sustained zero-order release of one or more biologic drugs. In some embodiments, this disclosure provides methods of localized delivery of one or more biologic drugs to a patient. In some embodiments, this disclosure provides methods of treating (prophylactically or therapeutically) a disease in a patient. In some embodiments, this disclosure provides methods of improving graft retention in a patient. Methods provided herein can include administering to a patient a DDS as described herein. Methods provided herein can also include removal of the DDS. Removal of the DDS can be following complete release of the one or more biologic drugs, following partial release of the one or more biologic drugs, and/or based upon a clinician's determination that sufficient amounts of the one or more biologic drugs have been delivered.

A patient can include both mammals and non-mammals. Mammals include, for example, humans; nonhuman primates, e.g. apes and monkeys; cattle; horses; sheep; rats; mice; pigs; and goats. Non-mammals include, for example, fish and birds. In some embodiments a patient is a human.

Methods of localized delivery of one or more biologic drugs to a patient can include administering to a patient a DDS as described herein at a topical surface. A DDS can be administered under invasive conditions that allow the DDS to provide sustained zero-order release of one or more biologic drugs at the implanted tissue. A tissue includes, without limitation, the skin, the nostrils, the lips of the mouth, the eye, the ears, the trachea, the stomach, the genital area, or the anus. In some embodiments, a tissue includes the eye (e.g., intraocular structures). For example, intraocular structures of the eye include the uvea, retina, and trabeculum. A DDS can be administered under non-invasive conditions that allow the DDS to provide sustained zero-order release of one or more biologic drugs at the topical surface. A topical surface includes, without limitation, the skin, the nostrils, the lips of the mouth, the eye, the ears, the trachea, the stomach, the genital area, or the anus. In some embodiments, a topical surface includes the eye (e.g., the ocular surface). For example, topical surfaces of the eye include the eyelid, conjunctiva, conjunctival fornix, and cornea.

In some embodiments, localized delivery of one or more biologic drugs (e.g., anti-VEGF) is effective to treat choroidal neovascularization, diabetic macular edema, and ocular surface conditions (e.g., corneal neovascularization, pterygium, and high-risk penetrating keratoplasty). In some embodiments, one or more biologic drugs (e.g., anti-TNF-α) are effective to treat corneal alkali burn (e.g., reduces inflammation, neovascularization, corneal opacity, perforation, and eyelid fibrosis), dry eye (e.g., improves tear volume, corneal surface regularity, and goblet cell density, and protects limbal stem cells), glaucoma (e.g., prevents corneal neovascularization and suppresses subconjunctival wound healing after trabeculectomy) and/or and retinal ganglion cell apoptosis.

Methods of treating (prophylactically or therapeutically) a disease in a patient can include administering to a patient a DDS as described herein to treat a topical disease. As used herein, a topical disease includes any disease for which the symptoms manifest on a topical surface (e.g., the eye or skin) of the patient and can be treated with a topical application of one or more biologic drugs. In some embodiments, the topical disease is a disease of the eye. Diseases of the eye include both ocular surface diseases and intraocular (retina, uvea) pathologies. Diseases of the eye can involve the eyelid, conjunctiva, cornea, uvea, retina, and trabeculum. Examples of eye diseases include, without limitation, glaucoma, corneal neovascularization, pterygium, high-risk penetrating keratoplasty, neurotrophic keratopathy, dry eye, alkali burn, and anterior uveitis.

In some embodiments, a disease is inflammation of a topical surface. The inflammation can be independently occurring or the inflammation can be a result or side effect of another pathology. For example, the inflammation can be ocular inflammation related to ocular surface diseases, traumas (e.g., burns), or autoimmune diseases (e.g., Stevens-Johnson disease, rheumatoid arthritis, Crohn disease, peripheral ulcerative keratitis, cicatricial pemphigoid, etc.).

Methods of improving graft retention in a patient can include administering to a patient a DDS as described herein at a topical surface of a graft. In some embodiments, a graft can include a skin graft or a keratoplasty. A skin graft can be due to, for example, trauma (e.g., burns or wounds), infection (e.g., necrotizing fasciitis or purpura fulminans), any surgery that may require skin grafts for healing to occur (e.g., removal of skin cancers) and/or autoimmune disease. Keratoplasty includes any surgery carried out on the cornea, including corneal transplantations in which a damaged or diseased cornea is replaced by corneal graft (e.g., penetrating keratoplasty, lamellar keratoplasty, Boston keratoprosthesis, AlphaCor implantation, and osteo-odonto-keratoprosthesis).

Administration of a DDS described herein is a non-invasive. Non-invasive routes of administration include, for example, placement of a DDS in the conjunctival fornix (e.g., the lower eyelid fornix or the upper eyelid fornix), subconjunctival space, skin, genital track, and/or mucosa in the mouth or in the cervix. In some embodiments, a DDS is administered in the lower lid fornix.

The invention will be further described in the following examples, which do not limit the scope of the invention described in the claims.

EXAMPLES

Example 1

A Drug Delivery System for Sustained Topical Administration of Anti-TNF-α Antibody This example describes the fabrication, evaluation and safety of a new drug delivery system (DDS) for topical anti-TNF-α antibody administration.

Materials and Methods

Preparation of the Drug Delivery System

A three-dimensional (3-D) porous polydimethylsiloxane (PDMS) block was prepared as described in Paschalis et al. (2014 *Transl Vis Sci Technol* 3 (5):4). Water dissolvable particles with a diameter between 100 and 300 μm were used to create the negative PDMS template. The particles were dissolved by agitation in 95° C. water for 3 hours resulting in an interconnected porous PDMS network (FIG. 1), as determined by non-destructive 3-D x-ray micro-computed-tomography (X-Tek HMXST225, Nikon Metrology Inc., Brighton, Mich., USA), and 3-D image reconstruction (VG-Studio Max 2.2, Volume Graphics, Heidelberg, Germany) (FIG. 1). The sponge-like microporous PDMS provided 50% cavitation volume and was sectioned into small segments of 5 mg (approximately 5×2×1 mm).

Figure 2:
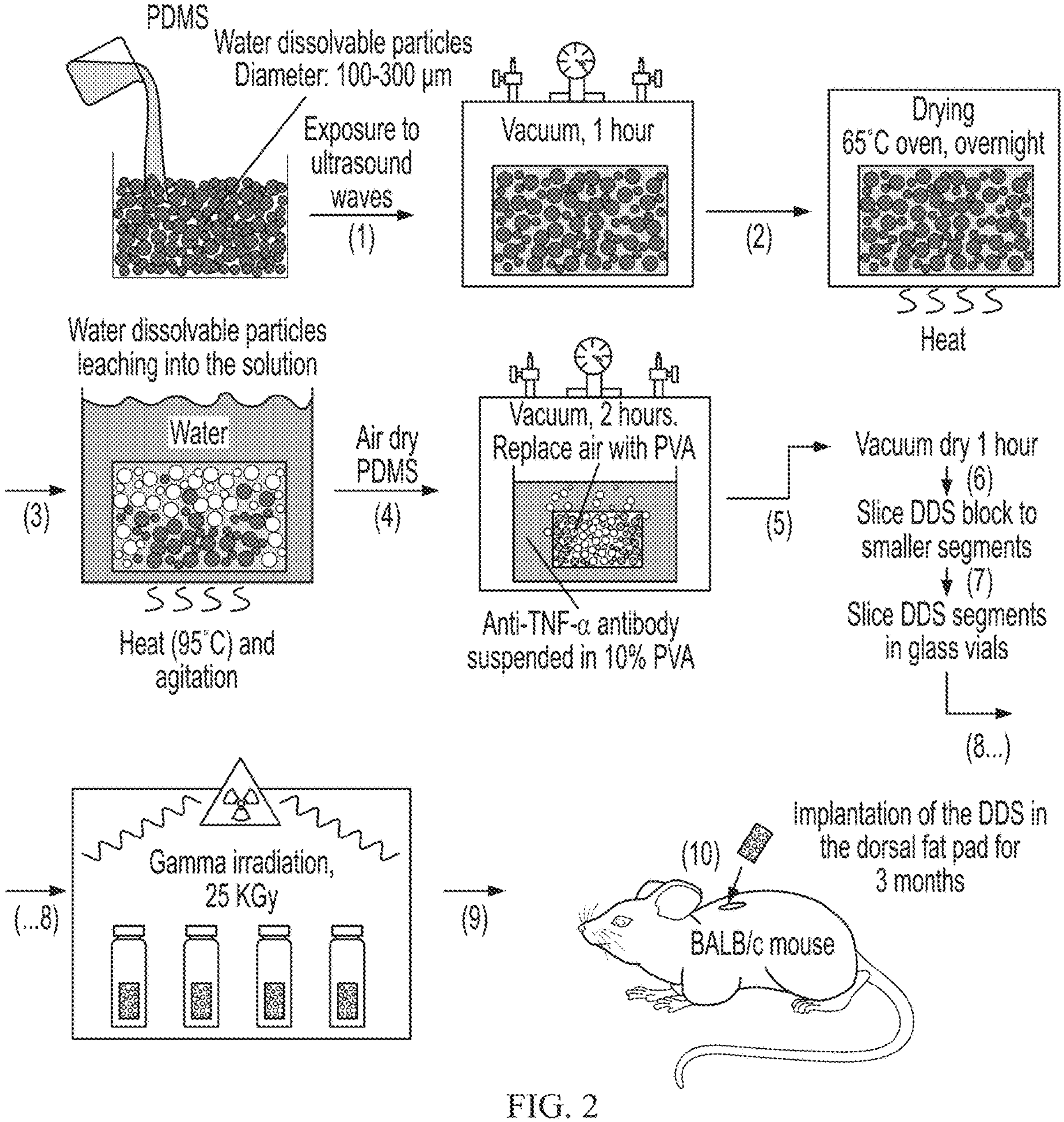
FIG. 2 is a schematic showing a manufacturing sequence of an anti-TNF-α drug delivery system (DDS).

Polyvinyl alcohol (PVA) 10% w/v loading polymer was prepared as follows: PVA powder (#363146-500G, Sigma Aldrich) was slowly added into DI water and stirred on a hotplate, heating up to 90-98° C. until the PVA powder was totally dissolved. The mixture was cooled to room temperature and infliximab lyophilized powder (a chimeric monoclonal an anti-TNF-α antibody) was suspended at a 34:1 weight/volume ratio (infliximab:PVA solution) resulting in a monoclonal anti-TNF-α antibody concentration of 5 mg/ml. The polymer was then loaded into the 3-D microporous PDMS using a vacuum chamber and air-dried (FIG. 2).

Infliximab-loaded PDMS (DDS) was stored at room temperature until use. Gamma-irradiation was applied to select DDSs used in the drug release assays and to all DDSs used in the in vivo assays given the need for sterilization of the device. A Cobalt-60 source was used to deliver a total dose of 25 KGy, which is the standard requirement for tissue sterilization.

Anti-TNF-α Stability and Release from the Drug Delivery Device

The stability and release of infliximab were evaluated using a commercially available sandwich enzyme-linked immunoassay (ELISA, Quantikine Human TNF-α Immunoassay, R&D Systems, Minneapolis, Minn.). The assay protocol was modified to include a 1-hour incubation at 37° C. to allow antigen-antibody binding between a known quantity of TNF-α (125 pg/mL) and the infliximab-eluted from the DDS. TNF-α bound by infliximab through antibody-antigen interaction is unable to bind to the capture antibody coating of the ELISA well and is, therefore, washed away during the subsequent steps of the assay. The remaining TNF-α in the solution, which was not bound by anti-TNF-α antibody, is then measured using the standard steps of the assay (Ikeda et al., 2012 *American Journal of Health-System Pharmacy* 69 (17):1509-12; Robert et al., 2014 *International Journal of Pharmaceutical Compounding* 18 (5):418-26). The amount of TNF-α bound by infliximab is then calculated by subtraction from the initial amount of TNF-α loaded into each well. Anti-TNF-α antibody activity was quantified as the percentage of captured TNF-α (TNF-α inhibition): [125 pg/mL minus TNF-α concentration measured by ELISA] divided by 125 pg/mL. A standard curve was prepared with each assay using TNF-α concentrations between 0 pg/mL and 125 pg/mL. The percentage of TNF-α inhibition was compared to inhibition values for known infliximab concentrations varying between 0 and 5000 ng/mL. The relationship between infliximab concentration and TNF-α binding to the ELISA was modeled with the following standard curve (allometric equation): infliximab concentration $(y)=0.05426\times(\text{optical density})^{-4.51279}$, $R^2=0.99$. The infliximab standard curve remained within the validated detection range of TNF-α (15.6 pg/mL-1,000 pg/mL) for the ELISA. All measurements were performed in triplicate.

The stability of the anti-TNF-α antibody was assessed under different conditions. First, the anti-TNF-α/PVA loading polymer mixture was evaluated after dry storage for 1 week at 4° C. and 37° C. On the day of the assay, the anti-TNF-α/PVA loading polymer was diluted in normal saline to an infliximab concentration of 4 μg/mL, mixed 50:50 with 250 pg/mL TNF-α (effective concentration of 125 pg/mL of TNF-α) and incubated for one hour at 37° C. The percentage of unbound TNF-α in the soaking solution was evaluated using ELISA and the percentage of TNF-α inhibition was calculated as described above. Also, the DDS was evaluated after dry storage at room temperature (RT) or 37° C. for up to 4 weeks. The DDS was submerged and incubated in 400 μL of 125 pg/mL TNF-α for one hour at 37° C. and this soaking solution was used for the subsequent ELISA assay. For these assays, fresh infliximab solution (4 μg/mL, lyophilized powder dissolved in normal saline) was prepared on the day of the assay as a positive control.

Figure 3:
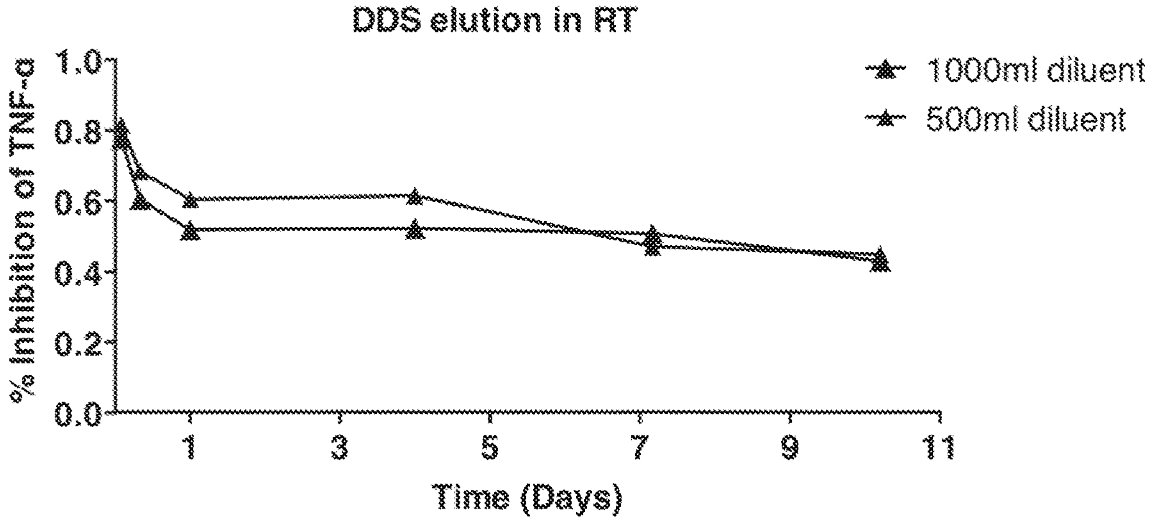
FIG. 3 is graph showing anti-TNF-α antibody release after continuous aqueous exposure of the drug delivery system. Quantification of released anti-TNF-α antibody was obtained through evaluation of TNF-α inhibition using a validated ELISA protocol. The volume of soaking solution (500 μL and 1000 μL) used to submerge the DDS did not have a significant impact on the measured release of anti-TNF-α antibody. As such, 500 μL soaking solution was used for all subsequent assays.

Sham PVA and sham DDS (without infliximab) were used as controls to ensure that the polymers did not adsorb or neutralize significant amounts of TNF-α. Sham PVA (PVA 10% without infliximab) was prepared and stored at 4° C. for 1 week, FIG. 3A. On the day of the assay, sham PVA was diluted in normal saline using the same dilution factor used for anti-TNF-α/PVA. The diluted sham PVA was mixed with TNF-α, incubated for one hour at 37° C. and used for the subsequent ELISA. Sham DDS were prepared, sectioned into 5 mg segments and stored at RT for 4 weeks prior to being assayed. Using an identical technique to infliximab loaded DDS, sham DSS segments were submerged and incubated in 400 μL of 125 pg/mL TNF-α solution for one hour at 37° C. The soaking solution was used for the subsequent ELISA.

Three segments of the DDS were used to assess drug release and stability after serial assays and wet-dry cycles over a 4-week period. After 1 or 2 weeks of dry storage at RT or 37° C., the segments were incubated with 125 pg/mL TNF-α at 37° C. for an hour. The soaking solution was used for the ELISA assay while the DDS segments were recovered, air-dried and stored at RT until the next assay. At this time, these segments were again incubated in 125 pg/mL TNF-α and the soaking solution was analyzed using ELISA.

To assess the drug-eluting properties of the DDS, 5 mg segments of the polymer were sequentially soaked in either 500 μL or 1000 μL of 0.9% normal saline and incubated at 37° C. for a 10-day period. As the volume of soaking solution did not significantly alter the release of infliximab (FIG. 3), all subsequent experiments were performed using 500 μL of soaking solution. Wherein infliximab is known to completely dissolve at a concentration of 10 mg/mL (Jansen Biotech, Dec. 16, 2014 *Remicade product monograph*), the expected amount of infliximab present in the DDS would only achieve concentrations in the μg/mL scale. Thus, the 500 μL volume of achieves sink conditions.

Non-gamma-irradiated and gamma-irradiated DDS segments were each sequentially transferred to fresh soaking solution at predetermined time-points over a one-month period. These included 3 and 24 hours as well as 2, 4, 6, 8, 10, 12, 15, 17, 20, 22, 25, 28 and 31 days after preparation. The different soaking solutions were stored at 4° C. until the day of the assay. Each soaking solution, which contained infliximab released from the DDS, was allowed to react with equal volume of 250 pg/mL TNF-α (final TNF-α concentration of 125 mg/mL) for one hour at 37° C. prior to proceeding with the ELISA assay using the standard protocol. This drug-elution experiment was repeated using non-gamma-irradiated and gamma-irradiated DDS that had previously been stored at RT or 4° C. for 1 year.

Given the limitations in quantifying the early release of high concentrations of infliximab using ELISA, quantification of infliximab protein eluted from the DDS was also performed using fluorescence spectroscopy with measurement of the infliximab fluorescence signal at 340 nm, using an excitation wavelength of 260 nm. First, the fluorescence measurements were performed on the 3-hour soaking solutions of 1-year old non-gamma-irradiated DDS as described above for the ELISA experiment. As well, real-time elution characteristics were evaluated using repeated fluorescence measurements over 3.5 hours of freshly prepared DDS placed inside a 1 cm×1 cm quartz cuvette containing 1.5 mL of 0.9% normal saline.

In Vivo Tolerance of the Drug Delivery Device

In vivo studies were approved by the Animal Care Committee of the Massachusetts Eye and Ear Infirmary. All animal-based procedures were performed in accordance with the Association For Research in Vision and Ophthalmology Statement for the use of Animals in Ophthalmic and Vision Research, and the National Institutes of Health Guidance for the Care and Use of Laboratory Animals.

All procedures were performed under general anesthesia using intraperitoneal ketamine (120 mg/kg, Putney Inc, Portland, Me.) and xylazine (20 mg/kg, Vedco Inc, St Joseph, Mo.) as described in Cade et al. (2014 *Cornea* 33 (4):382-9). Postoperative analgesia was provided using subcutaneous buprenorphine hydrochloride (0.05 mg/kg, Buprenex Injectable, Reckitt Benckiser Healthcare Ltd, United Kingdom).

In order to assess the in vivo safety, sections of the gamma-irradiated DDS were surgically implanted in the subcutaneous space of the dorsal fat pad in two BALB/c male mice and kept in situ for 3 months. Sham DDS without anti-TNF-α antibody was implanted in 2 separate BALB/c male mice as polymer controls. At 3 months, the DDS were explanted for further clinical and histopathologic analysis. The DDS and surrounding tissue was sectioned and stained with hematoxylin-eosin and Masson trichrome.

Statistical Analysis

Statistical analysis was performed using GraphPad Prism software (San Diego, Calif.). The inhibition of TNF-α by released infliximab was compared between time point and storage conditions using the nonparametric Kruskal-Wallis (KW) test. Dunn's multiple comparisons test was performed for each pair of the testing conditions if the p-value was below 0.05. Per convention, a two-tailed p-value below 0.05 was defined as being statistically significant. Bonferroni correction was applied as appropriate.

Results

Stability Evaluation of Drug Delivery Device

Figure 4:
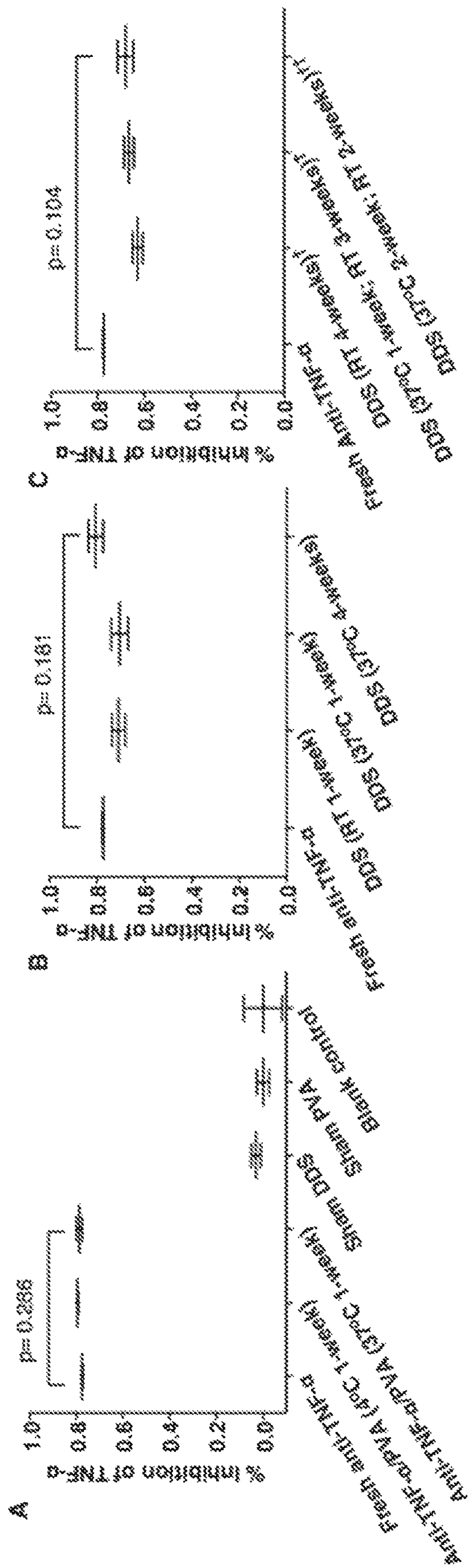
FIGS. 4A-C are series of graphs showing stability of anti-TNF-α antibody in the drug delivery system. A) Infliximab in polyvinyl alcohol (4 μg/mL) following 1 week at 4 or 37° C. has similar TNF-α binding affinity and inhibition when compared to freshly prepared 4 μg/mL infliximab. TNF-α inhibition with and without blank PVA or PDMS is negligible, demonstrating that neither polymer adsorbs TNF-α nor interfere with the assay; B) Infliximab in PDMS is stable after 1 week at RT as well as 1 and 4 weeks at 37° C.; C) Stability of anti-TNF-α loaded PDMS after 4 weeks at RT or 37° C. following repeated cycles of incubations in 125 pg/mL TNF-α solution and air-drying († one cycle, †† two cycles).

Quantification of infliximab, performed using a validated ELISA assay (Ikeda et al., 2012 *American Journal of Health-System Pharmacy* 69 (17):1509-12), revealed stable binding to TNF-α following storage in various conditions. Infliximab-PVA (4 μg/mL) stored for 1 week at either 4° C. or 37° C. had similar TNF-α inhibition when compared to freshly prepared infliximab (4 μg/mL) with TNF-α inhibition of 79.4%+/−0.2%, 78.7%+/−1.3% and 77.4%+/−0.1%, respectively (p=0.286; KW-test). PVA without infliximab did not show any inhibition of TNF-α (0.0%+/−2.9%) (FIG. 4, A).

The 5-mg DDS segments stored at RT or 37° C. for 1 week inhibited 71%+/−3% and 70%+/−3% of the TNF-α, respectively. The level of TNF-α inhibition after 4 weeks at 37° C. was not significantly changed (80.5%+/−3%, p=0.181; KW-test). Further, sham DDS (without anti-TNF-α) did not lead to significant inhibition of TNF-α (3.0%+/−1.9%) (FIG. 4, B). DDS, stored at RT and/or 37° C. for 4 weeks, continued to show 63 to 68% inhibition of TNF-α despite previous repeated dry-wet cycles and incubation with TNF-α solution (p=0.104; KW-test) (FIG. 4, C).

Anti-TNF-α Release from Drug Delivery Device

Figure 5:
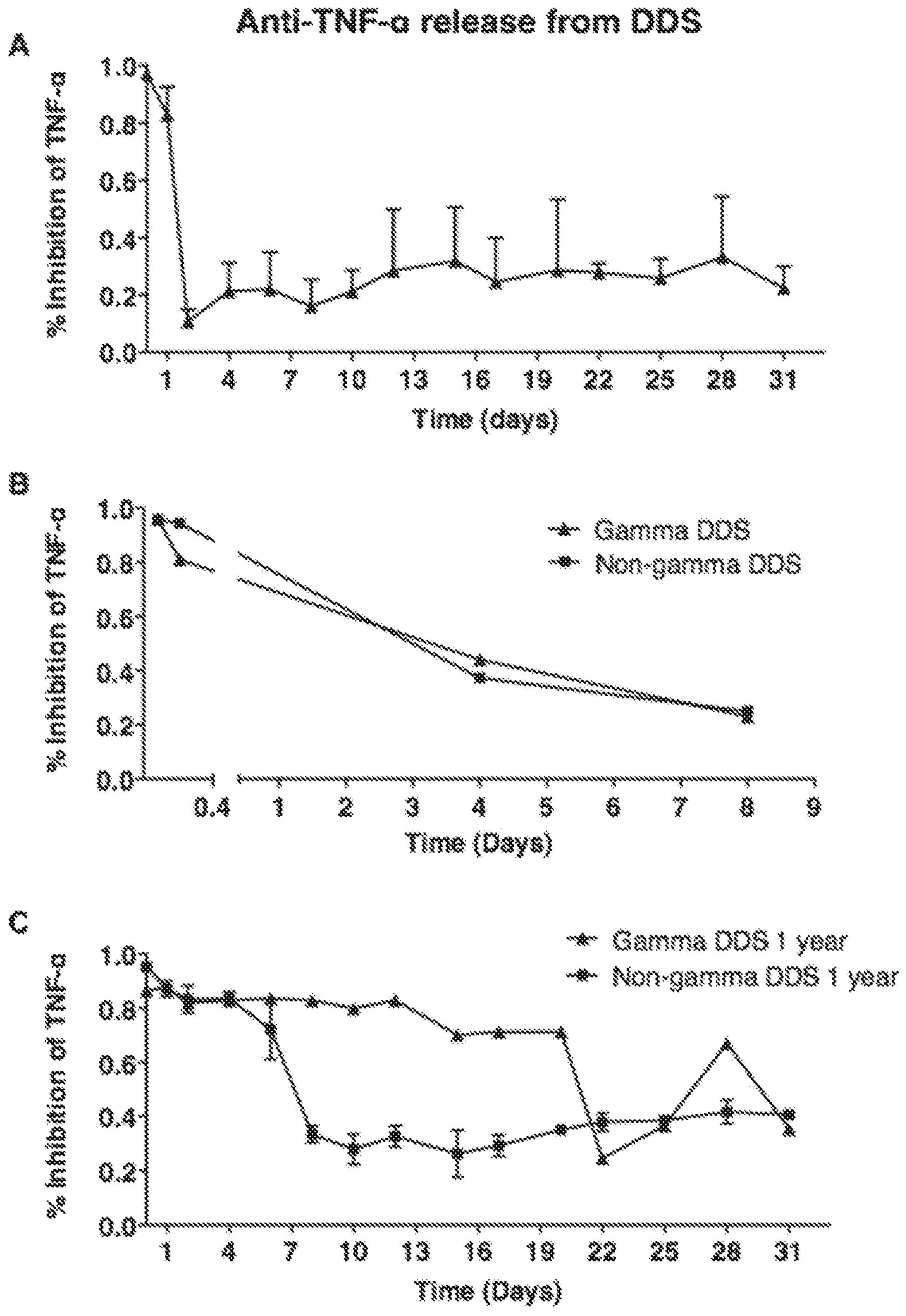
FIGS. 5A-C are series of graphs showing Anti-TNF-α antibody release after continuous aqueous exposure of the drug delivery system. A) The release of biologically active anti-TNF-α antibody from the drug delivery system (DDS) over 31 days is quantified as the relative inhibition of TNF-α (125 pg/mL). Due to burst release of anti-TNF-α antibody, TNF-α inhibition was almost complete after the initial 3-hour soaking period. High levels of anti-TNF-α antibody were released in the next 24 hours, followed by lower but stable zero-order-release for the subsequent 30 days. B) Gamma-irradiation with 25 KGy did not impede the release characteristics or the anti-TNF-α antibody or the binding affinity when compared with non gamma-irradiated DDS. C) After 1 year of shelf storage, non gamma-irradiated as well as gamma-irradiated DDS showed preserved inhibition of TNF-α. The release curve shows prolongation of the initial burst release of anti-TNF-α antibody, which is particularly marked for the gamma-irradiated DDS.

As shown in FIG. 5, the release of biologically active anti-TNF-α antibody from the DDS in the first 3 hours of soaking was significant. TNF-α inhibition was almost complete (96.9%+/−0.8%) and exceeded the lower detection limit of the assay. At 24 hours, release of infliximab remained high with 82.8%+/−9.8% inhibition of TNF-α, corresponding to an infliximab release of 4.21 μg/mL/day. Lower levels of drug release occurred at zero-order kinetics for the following 30 days. During this period (days 2 to 31), average TNF-α inhibition was 24%+/−6% and corresponded to infliximab release of 2.46+/−0.58 ng/mL/day (FIG. 5).

Gamma-irradiated DDS had similar infliximab release and TNF-α inhibition characteristics when compared to non gamma-irradiated DDS (FIG. 5, B). Further, non gamma-irradiated and gamma-irradiated DDS that had been kept at RT for 1 year showed a retained ability to release biologically active infliximab (FIG. 5, C). The release curve showed high levels (>80%) of TNF-α inhibition for the first 4 days and 12 days of continuous aqueous exposure for the non gamma-irradiated and gamma-irradiated DDS, respectively. In contrast, freshly prepared DDS only exhibited this level of TNF-α inhibition over the first 24 hours.

Figure 6:
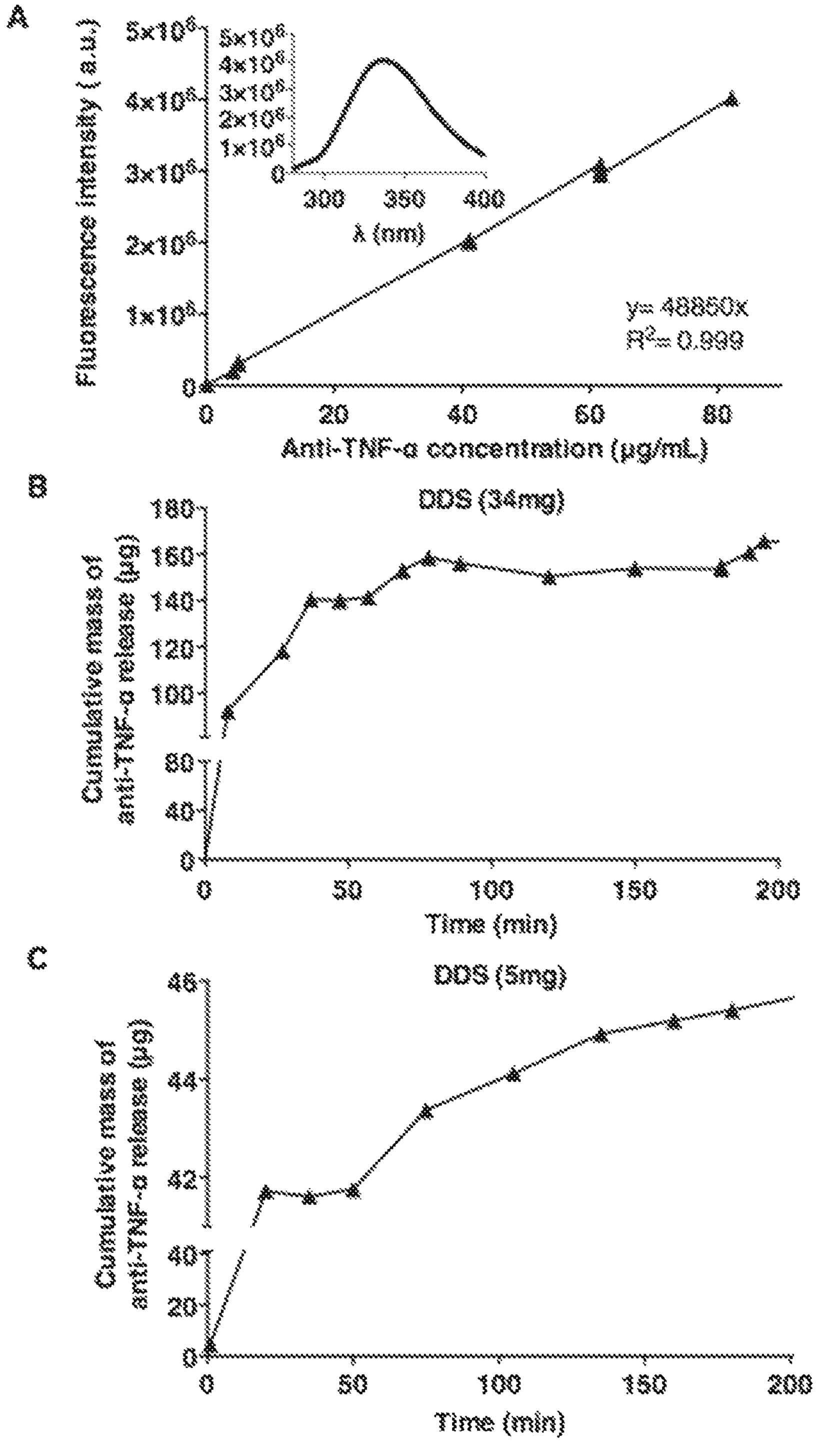
FIGS. 6A-C are series of graphs showing Release of anti-TNF-α antibody from the drug delivery system using fluorescence spectroscopy. A) Fluorescence calibration curve for anti-TNF-α antibody in normal saline buffer (excitation wavelength of 260 nm, monitoring wavelength (λ) of 340 nm). The fluorescence signal linearly correlates to concentrations of freshly prepared anti-TNF-α antibody between 0 to 80 μg/mL (R2>0.99). The inset illustrates the fluorescence spectrum for infliximab at a concentration of 82 μg/mL (excitation λ=260 nm). B) Time-based release of anti-TNF-α antibody from a 5 mg total weight DDS placed into 1.5 mL of normal saline at room temperature as measured by fluorescence. C) Time-based release of anti-TNF-α antibody from a 34 mg total weight DDS placed into 1.5 mL of normal saline at room temperature as measured by fluorescence.

Using an excitation wavelength of 260 nm, the fluorescence signal of freshly prepared infliximab in normal saline at 340 nm was linearly correlated to infliximab concentrations between 0 to 80 μg/mL ($R^2$>0.99) (FIG. 6, A). One-year old DDS released 52+/−15 μg of infliximab after 3 hours of soaking in normal saline. Real-time monitoring of infliximab release from two different sizes of DDS (5 mg and 35 mg total weight) revealed that the burst release occurred within the first few minutes of soaking and that slow elution continued thereafter (FIG. 6, B-C). The burst of infliximab release is thought to be related to the infliximab/PVA found on the surface of the polymer, while the subsequent slower release rates relates to diffusion of infliximab from inside the PDMS polymer.

In Vivo Tolerance of the Drug Delivery Device

Figure 7:
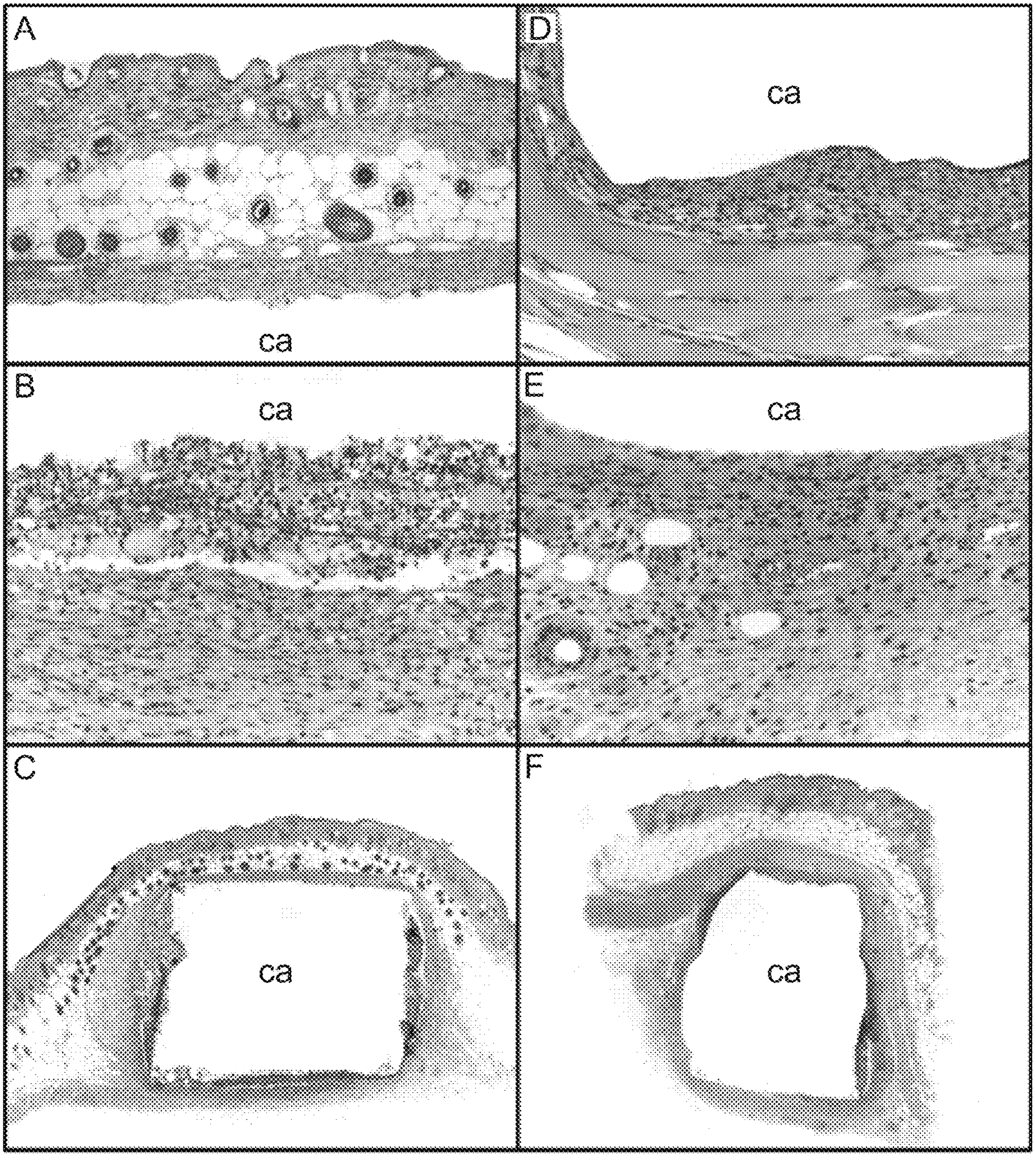
FIGS. 7A-F are series of microscope images showing histopathologic findings of implanted with anti-TNF-α antibody (A-C) DDS and control DDS (D-F). A) Masson trichrome stain discloses that the collagen of the dermis is blue. The subdermal fat bearing cross sections of hairs is uninflamed. Note the pseudocapsule lining the implant cavity (ca) below is lightly red staining and lacks blue staining collagen as well as prominent capillaries. B) Upon the inside surface of the pseudocapsule below rests an exudative inflammatory process with suspended acute and chronic inflammatory cells. Similar cells are also present in the more compact fibroblastic pseudocapsule devoid of capillaries. DDS cavity (ca). C) Cavity of an explanted DDS (ca) that contained anti-TNF-α antibody. The implant encroaches on the subcutaneous fat with hairs and was located above the striated muscle. An inflammatory exudate with suspended cells is apparent multifocally, especially on the inside of the fibroblastic pseudocapsule at the lateral and vertically oriented edges. There is considerable myxoid change in the fat on the left adjacent to the cavity. Striated muscle is revealed as an uninflamed eosinophilic band below the cavity. D) More compact zone of cavity wall beneath striated muscle fibers below. E) Bland stromal cells and scattered mononuclear inflammatory cells constitute the wall delimiting the cystic cavity below. Several small capillaries can be seen in the wall. DDS cavity (ca). F) Low power photomicrograph of cavity (ca) that had a drug delivery system (DDS) without anti-TNF-α antibody. The epidermis and dermis are present on the top, beneath which is a layer of uninflamed fat. The implant is located beneath the subcutaneous musculature. (A, B, C, D, F, hematoxylin and eosin, ×50, ×200, ×200, ×50, ×200; E) Masson trichrome, ×100).

A DDS (5×2×1 mm in size) was implanted subcutaneously beneath the dorsal fat pad in two anesthetized BALB/c mice without complication. The mice were observed for three months and did not show evidence of clinical inflammation, infection, skin necrosis or systemic illness. After three months, the explanted DDS with and without anti-TNF-α antibody showed similar histopathological findings (FIG. 7). The implants were found to have been inserted either in a pre-muscular plane or underneath multiple layers of striated muscle cells. A thin and irregular translucent lamina of DDS residue was adherent to the tissue edges, but most of the device had been dislodged or dissolved during tissue processing. Fibroblastic proliferation was detected in the host tissues immediately surrounding the implants and manifested little evidence of collagen synthesis as revealed by the Masson trichrome stain which demonstrated the absence of blue stain interstitial fibrillar material (FIG. 7, A). The fibroblastic pseudocapsule was most compact at the superficial edge and looser at the base and lateral edges of the implant. The spindle cells responsible for the pseudocapsule appeared to be myofibroblasts in view of their cytoplasmic fuchsinophilia with the Masson trichrome stain. A mixed mononuclear and polymorphonuclear leukocytic inflammatory response was observed in multiple foci along the inner aspect of the fibrous pseudocapsule (FIG. 7, B). The implants with anti-TNF-α antibody (FIG. 7, A-C) showed somewhat greater inflammation immediately abutting the DDS. The implants without anti-TNF-α antibody (FIG. 7, D-F) had a slightly greater presence of capillaries in the vicinity of the implant. In one of these infliximab-loaded implants, a focus of myxoid reaction containing acute and chronic inflammation was seen in the adjacent fat. Granulomatous zones were not observed around or near the implants.

Conclusion

These results demonstrate that anti-TNF-α DDS made of PDMS/PVA polymers can be prepared and sterilized using gamma-irradiation, providing an initial burst of biologically active antibody followed by zero-order release for up to 31 days in vitro.

Example 2

In Vitro Characterization for Anti-TNF-α Antibody Elution in Mice

In vitro characterization for anti-TNF-α antibody elution was completed and safety was assessed in mice. Preliminary in vivo results in mice with ocular burns were performed.

Drug loaded and sham DDS were implanted in the dorsal fat of Balb/c mice after corneal alkali burn with 1N NaOH. The eyes were imaged 3 months after burn.

Figure 8:
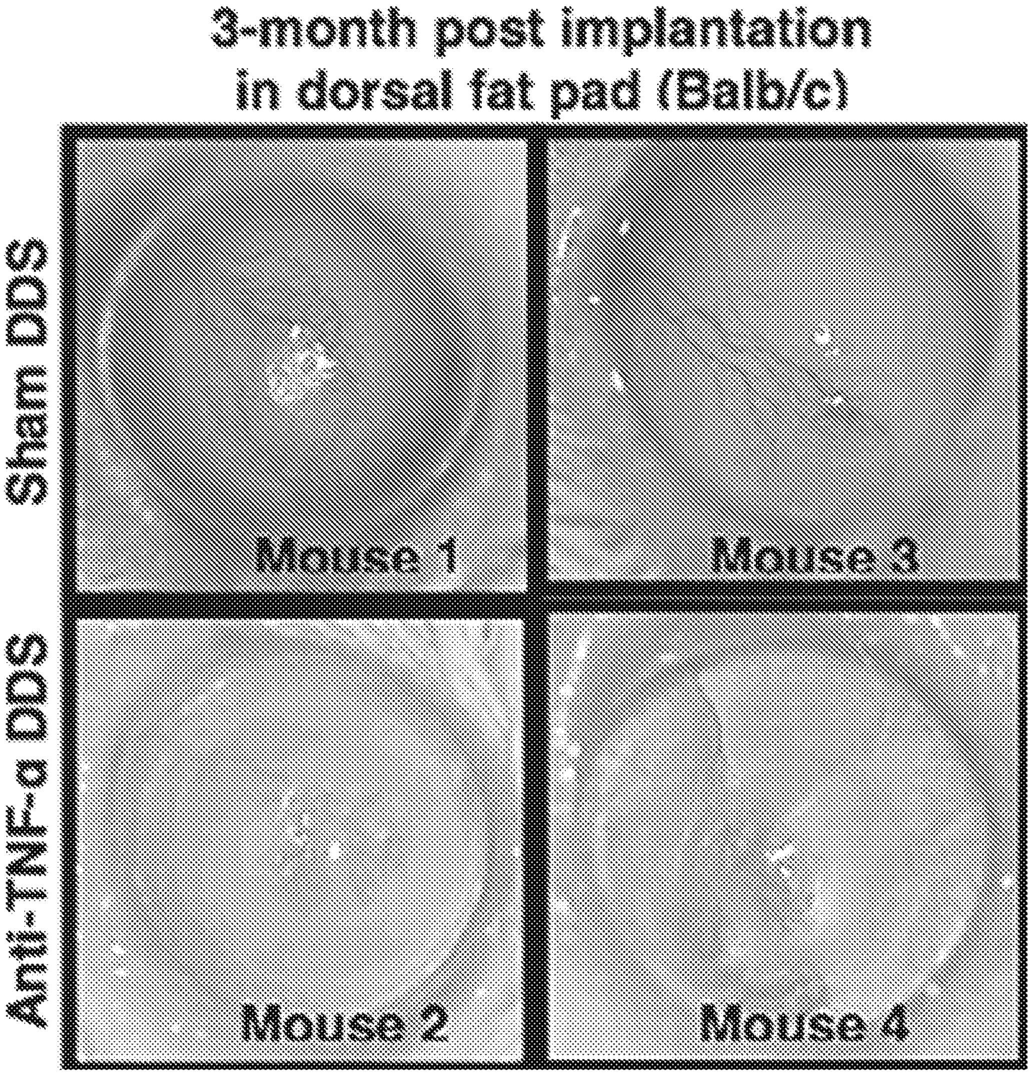
FIG. 8 is a series of images showing implantation of sham and anti-TNF-α loaded DDS in the dorsal fat of Balb/c mice after corneal alkali burn with 1N NaOH. Eyes were imaged 3 months after burn.

Sham DDS treated mice exhibited significantly more corneal neovascularization, edema and lens opacity compared to anti-TNF-α DDS treated mice (FIG. 8).

These results demonstrated that an anti-TNF-α loaded DDS provides sufficient drug elution to treat corneal alkali burn.

Example 3

In Vitro Characterization for Anti-TNF-α Antibody Elution in Rabbits

In vitro characterization for anti-TNF-α antibody elution was completed in rabbits. Preliminary in vivo results in rabbits with ocular burns were performed.

Drug loaded and sham DDS were implanted in the conjunctiva of the lower lid of rabbits after corneal alkali burn with 2N NaOH. The eyes were imaged 3 weeks after burn.

Figure 9:
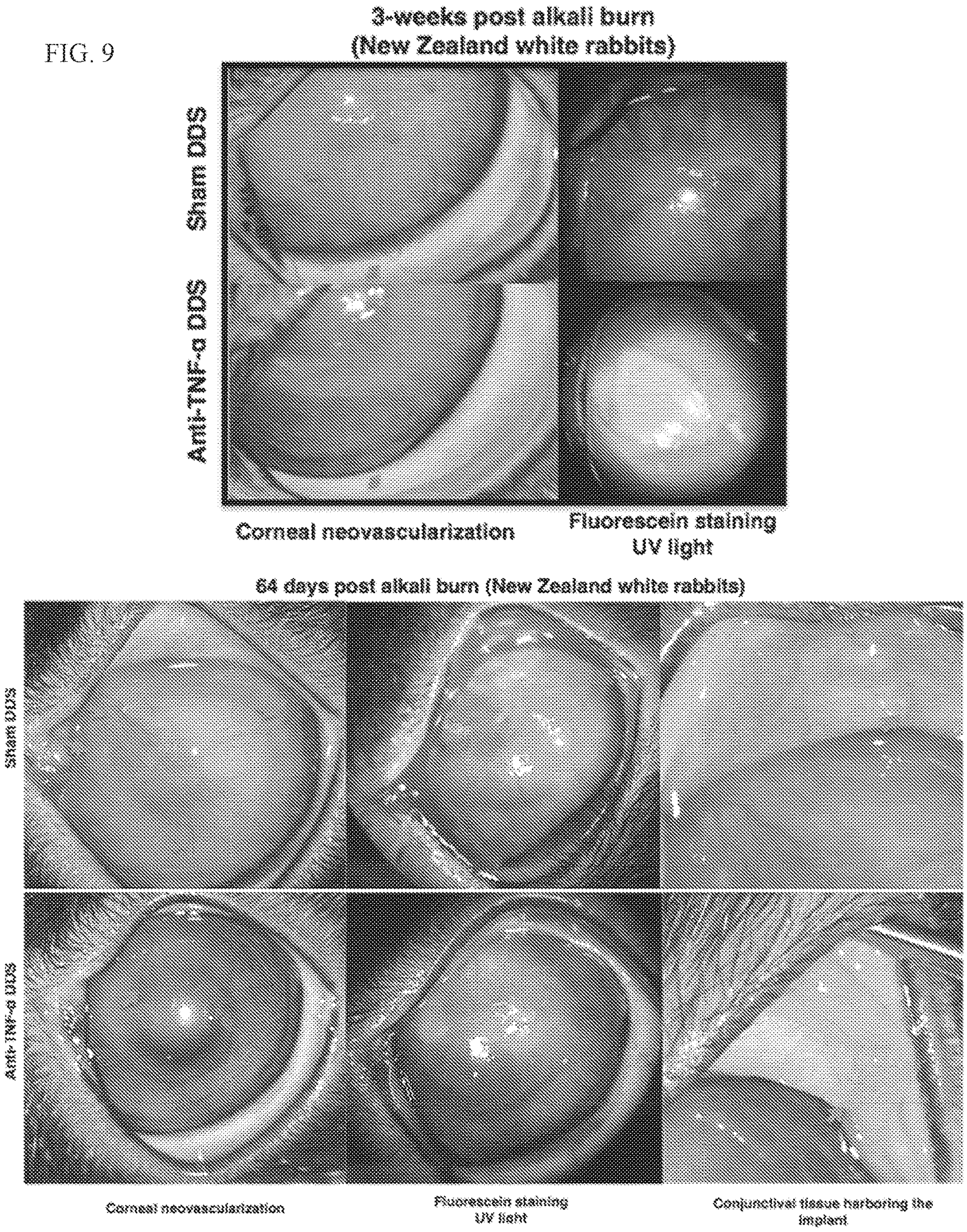
FIG. 9 is a series of images showing corneal neovascularization, epithelial defects and conjunctival inflammation after implantation of sham and anti-TNF-α loaded DDS in the conjunctiva of the lower lid of rabbits after corneal alkali burn with 2N NaOH. Eyes were imaged 3 weeks and 64 days after burn.

Rabbit eyes treated with sham polymer showed significant corneal opacification and neovascularization (arrows) 3 weeks after the burn compared to rabbits that received anti-TNF-α loaded polymers (FIG. 9). Sham treatment led to reduced re-epithelialization (FIG. 9).

These results demonstrated that an anti-TNF-α loaded DDS provides sufficient drug elution to treat corneal alkali burn.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A drug delivery system comprising:

a porous 3-dimensional hydrophobic polydimethylsiloxane (PDMS) polymer scaffold having at least 50% cavitation volume and at least 50% w/v of a hydrophilic poly(vinyl alcohol) (PVA) hydrogel loaded within the cavities of the porous 3-dimensional hydrophobic PDMS polymer scaffold;

wherein the porous 3-dimensional hydrophobic PDMS polymer scaffold comprises an interconnected network of monodispersed pores that are 100-300 μm in diameter;

wherein the hydrophilic PVA hydrogel comprises one or more anti-tumor necrosis factor alpha (TNF-α) antibodies consisting of infliximab or etanercept; and wherein the one or more anti-TNF-α antibodies are released from the drug delivery system at a zero-order release rate of 1 ng/mL/day to 10 ng/mL/day.

2. The drug delivery system of claim 1, wherein the PVA has a MW of 85,000-124,000 Da.

3. The drug delivery system of claim 1, wherein the hydrogel further comprises an anti-vascular endothelial growth factor (VEGF) agent.

4. The drug delivery system of claim 1, wherein the hydrogel comprises 5 mg/ml of the one or more anti-TNF-α antibodies.

5. The drug delivery system of claim 1, wherein the drug delivery system is 5×2×1 mm.

6. The drug delivery system of claim 1, wherein the drug delivery system is sterilized using gamma-irradiation.

7. A method for providing sustained zero-order release of one or more anti-TNF-α antibodies to a patient, the method comprising:

administering to a patient a drug delivery system comprising a porous 3-dimensional hydrophobic PDMS polymer scaffold having at least 50% cavitation volume and at least 50% w/v of a hydrophilic PVA hydrogel loaded within the cavities of the porous 3-dimensional hydrophobic PDMS polymer scaffold;

wherein the porous 3-dimensional hydrophobic PDMS polymer scaffold comprises an interconnected network of monodispersed pores that are 100-300 μm; and wherein the hydrophilic PVA hydrogel comprises one or more anti-TNF-α antibodies consisting of infliximab or etanercept; and wherein the one or more anti-TNF-α antibodies are released from the drug delivery system at a zero-order release rate of 1 ng/mL/day to 10 ng/mL/day.

8. The method of claim 7, wherein sustained release comprises an extended time period of 1 month.

9. The method of claim 7, wherein the release of one or more anti-TNF-α antibodies comprises a release of at least 70% of the one or more anti-TNF-α antibodies.

10. The method of claim 7, wherein release of the one or more anti-TNF-α antibodies occurs at 2.5 ng/mL/day.

11. A method for providing localized delivery of one or more anti-TNF-α antibodies to a patient, the method comprising:

administering to a patient a drug delivery system comprising a porous 3-dimensional hydrophobic PDMS polymer scaffold having at least 50% cavitation volume and at least 50% w/v of a hydrophilic PVA hydrogel loaded within the cavities of the porous 3-dimensional hydrophobic PDMS polymer scaffold;

wherein the porous 3-dimensional hydrophobic PDMS polymer scaffold comprises an interconnected network of monodispersed pores that are 100-300 μm in diameter; and wherein the hydrophilic PVA hydrogel comprises one or more anti-TNF-α antibodies consisting of infliximab or etanercept; and wherein the one or more anti-TNF-α antibodies are released from the drug delivery system at a zero-order release rate of 1 ng/mL/day to 10 ng/mL/day.

12. The method of claim 11, wherein localized delivery of the one or more anti-TNF-α antibodies is effective to treat an eye disease selected from the group consisting of macular degeneration, diabetic macular edema, corneal neovascularization, pterygium, high-risk penetrating keratoplasty, corneal alkali burn, dry eye, and glaucoma.

13. A method for treating an eye disease in a patient, the method comprising:

administering to a patient a drug delivery system comprising a porous 3-dimensional hydrophobic PDMS polymer scaffold having at least 50% cavitation volume and at least 50% w/v of a hydrophilic PVA hydrogel loaded within the cavities of the porous 3-dimensional hydrophobic PDMS polymer scaffold;

wherein the porous 3-dimensional hydrophobic PDMS polymer scaffold comprises an interconnected network of monodispersed pores that are 100-300 μm in diameter; and wherein the hydrophilic PVA hydrogel comprises one or more anti-TNF-α antibodies consisting of infliximab or etanercept; and wherein the one or more anti-TNF-α antibodies are released from the drug delivery system at a zero-order release rate of 1 ng/mL/day to 10 ng/mL/day.

14. The method of claim 13, wherein the eye disease comprises a topical disease of the eye or ocular inflammation.

15. The method of claim 14, wherein the topical disease of the eye is selected from the group consisting of glaucoma, corneal neovascularization, pterygium, high-risk penetrating keratoplasty, neurotrophic keratopathy, dry eye, alkali burn, and anterior uveitis.

16. A method of improving eye graft retention in a patient, the method comprising:

administering to a patient a drug delivery system comprising a porous 3-dimensional hydrophobic PDMS polymer scaffold having at least 50% cavitation volume and at least 50% w/v of a hydrophilic PVA hydrogel loaded within the cavities of the porous 3-dimensional scaffold;

wherein the porous 3-dimensional hydrophobic PDMS polymer scaffold comprises an interconnected network of monodispersed pores that are 100-300 μm in diameter; and wherein the hydrogel comprises a hydrophilic PVA polymer and one or more anti-TNF-α antibodies consisting of infliximab or etanercept; and wherein the one or more anti-TNF-α antibodies are released from the drug delivery system at a zero-order release rate of 1 ng/mL/day to 10 ng/mL/day.

17. The method of claim 16, wherein the eye graft is a keratoplasty selected from the group consisting of penetrating keratoplasty, lamellar keratoplasty, keratoprosthesis, and osteo-odonto-keratoprosthesis.

18. The method of claim 7, wherein the patient is a human.

19. The method of claim 7, wherein the administering is non-invasive.

20. The method of claim 7, wherein the drug delivery system is administered at a topical surface.

21. The method of claim 20, wherein the topical surface is a lower eyelid fornix.

* * * * *

UNITED STATES PATENT AND TRADEMARK OFFICE

CERTIFICATE OF CORRECTION

PATENT NO. : 11,173,130 B2
APPLICATION NO. : 15/760699
DATED : November 16, 2021
INVENTOR(S) : Eleftherios Paschalis Ilios It is certified that error appears in the above-identified patent and that said Letters Patent is hereby corrected as shown below:

In the Claims

In Column 19, Line 28, in Claim 7, delete "μm;" and insert -- μm in diameter; --

Signed and Sealed this
Nineteenth Day of July, 2022

Katherine Kelly Vidal

Katherine Kelly Vidal
*Director of the United States Patent and Trademark Office*